United States Patent [19]

Houghton et al.

[11] Patent Number: 5,135,511
[45] Date of Patent: Aug. 4, 1992

[54] ASSEMBLY FOR ASPIRATING TISSUE, INCLUDING ADAPTER FOR SYRINGE

[75] Inventors: Frederick C. Houghton, Sussex; Richard G. Giddes, Edison, both of N.J.

[73] Assignee: Becton, Dickinson and Company, Franklin Lakes, N.J.

[21] Appl. No.: 571,053

[22] Filed: Aug. 22, 1990

[51] Int. Cl.⁵ ............................................. A61M 5/315
[52] U.S. Cl. .................................. 604/220; 604/218; 604/233; 604/228
[58] Field of Search ............... 604/218, 220, 221, 223, 604/227, 228, 233, 235

[56] References Cited

U.S. PATENT DOCUMENTS

| | | |
|---|---|---|
| 1,325,699 | 12/1919 | Oesterhaus . |
| 1,798,116 | 3/1931 | Brockway . |
| 2,369,304 | 2/1945 | Lewis . |
| 3,819,091 | 6/1974 | Hollender . |
| 3,835,835 | 9/1974 | Thompson et al. . |
| 3,990,446 | 11/1976 | Taylor .................. 604/227 |
| 4,248,225 | 2/1981 | Moore . |
| 4,263,911 | 4/1981 | McCormack et al. ......... 604/227 |
| 4,664,128 | 5/1987 | Lee . |
| 4,711,637 | 12/1987 | Leigh et al. . |
| 4,758,232 | 7/1988 | Chak . |
| 4,766,908 | 8/1988 | Clement . |
| 4,863,072 | 9/1989 | Perler ..................... 604/228 |
| 5,004,124 | 4/1991 | Stefaniak et al. ............ 604/228 |

FOREIGN PATENT DOCUMENTS

| | | |
|---|---|---|
| 0453011 | 11/1948 | Canada .................... 604/233 |
| 0687475 | 1/1940 | Fed. Rep. of Germany ...... 604/227 |

Primary Examiner—C. Fred Rosenbaum
Assistant Examiner—Ronald Stright, Jr.
Attorney, Agent, or Firm—John L. Voellmicke

[57] ABSTRACT

An adapter is provided for enabling the single-handed use of a syringe for aspiration. An assembly including such an adapter is also provided. The adapter includes an elongate body portion including a first end portion which functions as a thumb pad and a second end portion secured to the syringe barrel. A winged member is secured to the syringe plunger and includes a pair of flanges extending outside the adapter. The syringe plunger may be retracted using only one hand by pulling the flanges of the winged member with the index and middle fingers while maintaining the thumb upon the first end portion of the adapter.

9 Claims, 6 Drawing Sheets

ASSEMBLY FOR ASPIRATING TISSUE, INCLUDING ADAPTER FOR SYRINGE

BACKGROUND OF THE INVENTION

1. Field of the Invention

The field of the invention relates to assemblies for aspirating tissue from the body through the use of a syringe.

2. Brief Description of the Related Art

Various aspiration devices have been designed for obtaining tissue samples and other liquid samples. Many such devices include modified syringe assemblies. U.S. Pat. Nos. 2,369,304; 3,835,835; 4,248,225; 4,664,128; 4,711,637; and 4,758,232 disclose a number of aspiration devices which employ syringes. U.S. Pat. No. 2,369,304 discloses a ratchet and pawl assembly which maintains a piston in a selected position within a syringe barrel, thereby providing a desired vacuum within the barrel.

It is often desirable to be able to aspirate tissue using only one hand. This allows the other hand to be used for other purposes. U.S. Pat. Nos. 4,664,128; 4,664,908 and 3,819,091 disclose two different constructions which allow syringes to be employed in this manner.

SUMMARY OF THE INVENTION

It is an object of the invention to provide an assembly which allows the manipulation of a syringe plunger using only on hand.

It is another object to the invention to provide an adapter which is readily securable to a syringe barrel and converts it to an assembly which is easily operable using only one hand.

In accordance with these and other objects of the invention, a syringe adapter is provided which includes an elongate body portion having a longitudinal axis, a bottom wall and a pair of side walls adjoining the bottom wall. A first end portion is adjoined to the body portion and includes an exterior end surface extending substantially perpendicularly to the longitudinal axis of the body portion. A second end portion is adjoined to the body portion opposite from the first end portion and includes means for releasably engaging a flange of a syringe barrel. The adapter preferably includes first and second elongate members which are pivotable between a closed position, where the adapter engages the syringe barrel, and an open position. The first end portion of the adapter may include a living hinge which functions as a pivot. The second end portion of the syringe may be slotted in order to receive the flange of the syringe barrel. The adapter may have a generally cylindrical configuration when in the closed position with a pair of elongate, longitudinally extending slots extending through the walls of the adapter.

An assembly for aspirating tissue is also provided by the invention. The assembly includes a syringe barrel including a first distal end and a second proximal end, the distal end thereof including a tip portion and the proximal end including a flange. A piston is positioned within the syringe barrel and a plunger projects from said piston extending outwardly from the proximal end of the barrel. An extension tube is secured to the flange, and has a longitudinal axis extending substantially parallel to the longitudinal axis of the syringe barrel. The plunger is positioned at least partially within the extension tube and includes a radially projecting flange extending outside the extension tube. The extension tube includes an engagement surface located proximally of the radially projecting flange of the plunger, whereby the plunger can be withdrawn with one hand by causing one or more fingers to exert pressure upon the radially projecting flange of the plunger in the direction of the engagement surface of the extension tube while the thumb engages this engagement surface.

DETAILED DESCRIPTION OF THE INVENTION

Figure 1:
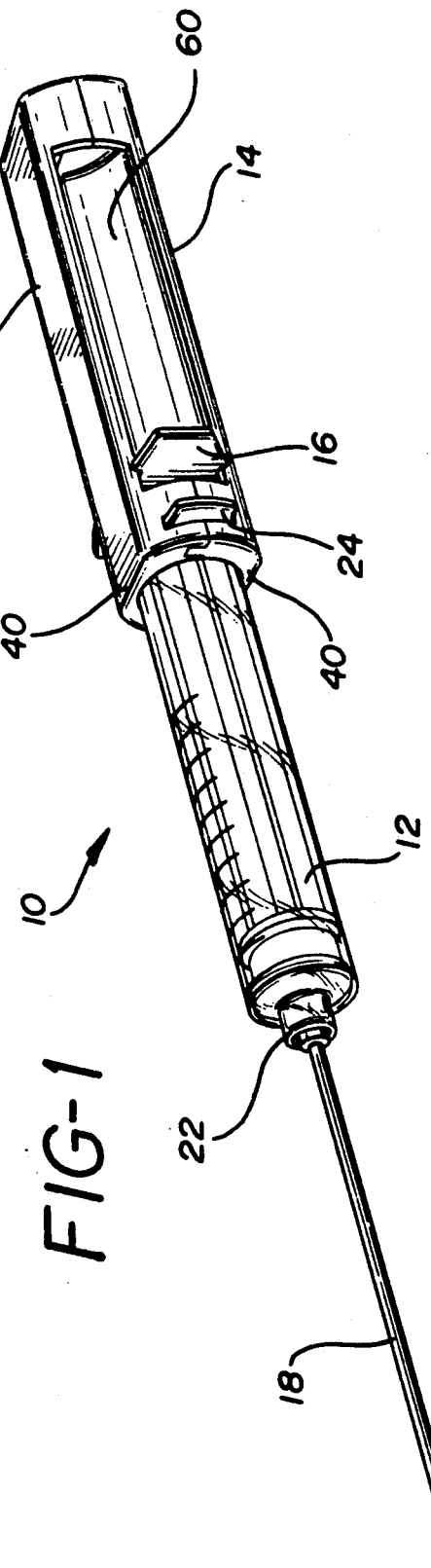
FIG. 1 is a perspective view of an assembly according to the invention showing the syringe plunger in the fully extended position.
Figure 2:
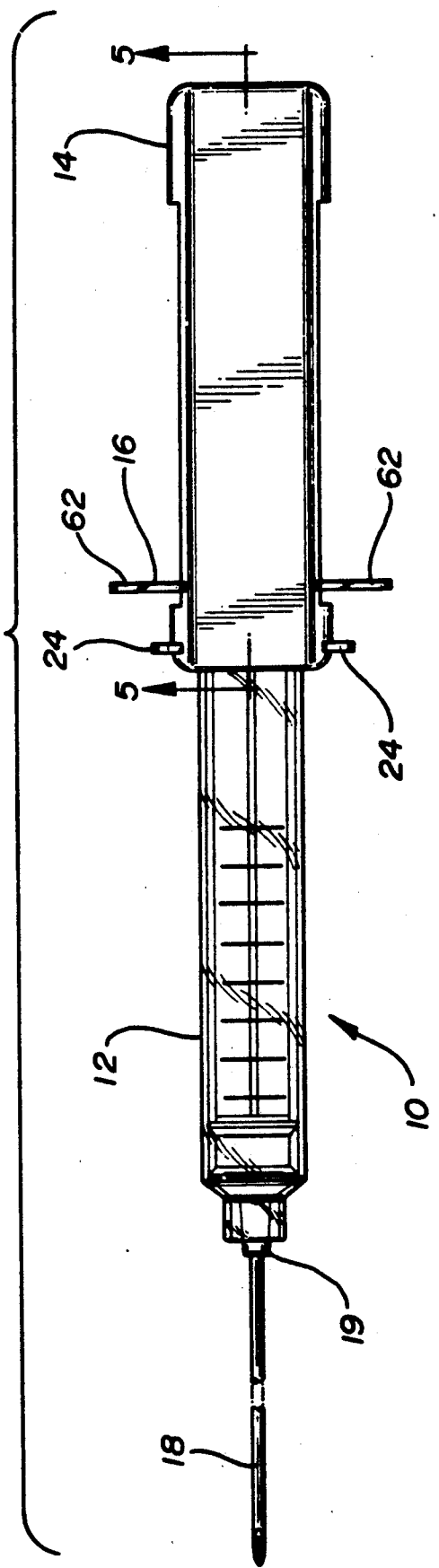
FIG. 2 is a top plan view of the assembly of FIG. 1.

An assembly 10 is provided for use in connection with needle aspiration biopsy or other procedures requiring aspiration. The assembly 10 includes a syringe 12, a preferably integrally molded adapter 14 secured to a barrel 20 of a syringe 12, and a winged member 16 secured to a syringe plunger 28. A needle assembly 17 is secured to the syringe. This assembly 10 is shown in FIGS. 1-2.

Figure 3:
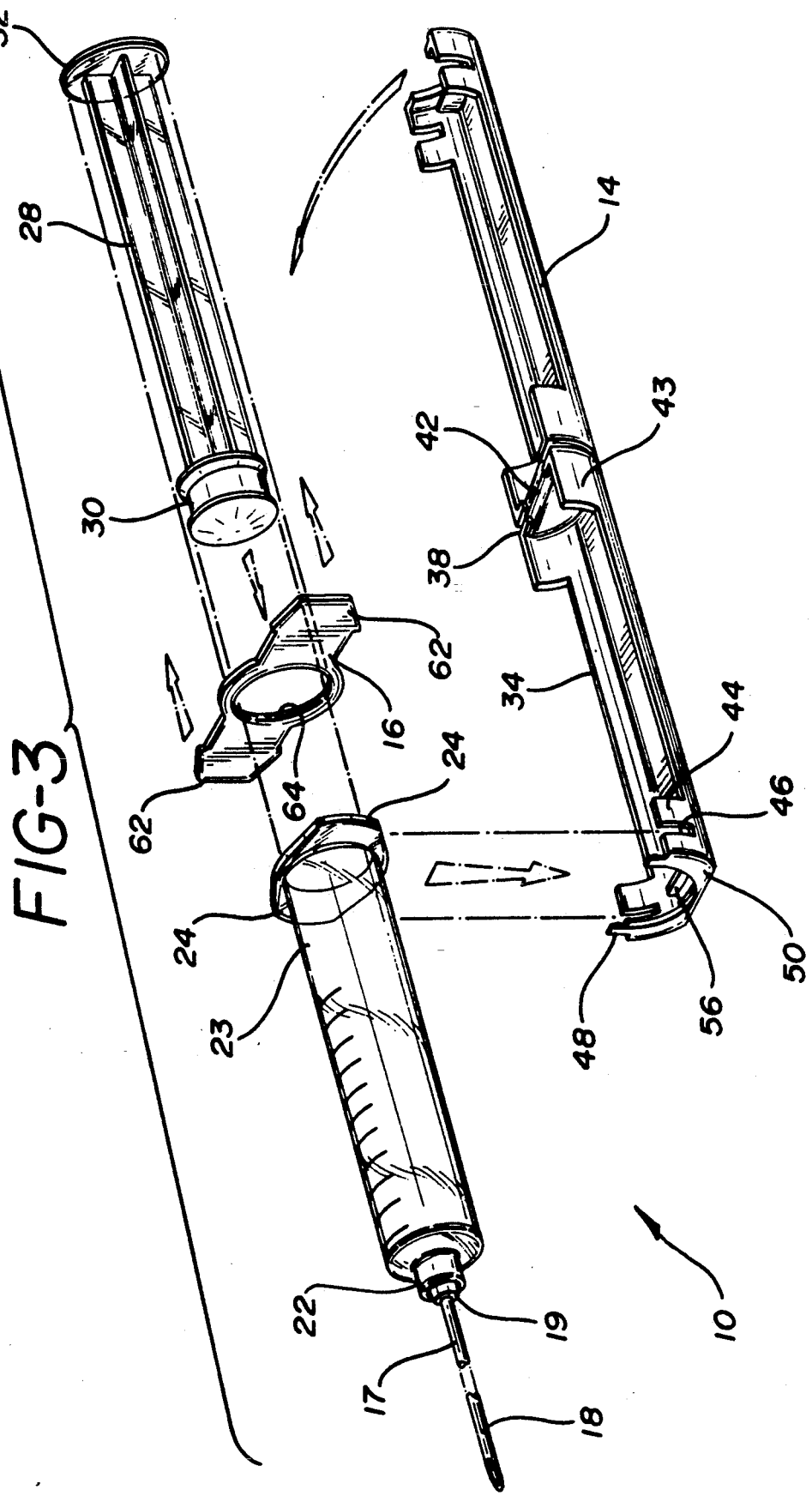
FIG. 3 is an exploded, perspective view of the assembly of FIG. 1.

The syringe 12 may be substantially conventional in construction, as shown in FIG. 3. It will be appreciated that the adapter 14 can be used in connection with syringes of different sizes or designs either in the form shown or as modified to conform to such sizes or designs.

The syringe 12 includes the cylindrical syringe barrel 20 having a distal end 21 including a tip portion 22 for engaging a hypodermic needle assembly and a proximal end 23 including a pair of flanges 24 extending radially with respect to the longitudinal axis of the barrel. The barrel is preferably transparent or translucent, and preferably includes graduations thereon which are indicative of volume. A hypodermic needle assembly 17 includes a needle 18 secured to a hub 19 which is secured to the syringe tip portion 22 by means of a locking luer type mechanism, a luer slip type engagement or the like.

For the purposes of the description of the present invention the term "distal end" is meant to refer to the end of the assembly closest to the needle or to the portion of the assembly where a needle assembly may be attached, whereas the term "proximal end" is meant to refer to the end of the assembly furthest from that portion of the assembly having the needle.

The syringe plunger 28 is at least partially positioned within the syringe barrel 20. The plunger 28 includes a piston 30 which sealingly engages the walls of the syringe barrel. The rear end of the plunger is defined by a radially projecting flange 32 in the form of a disk. In this preferred embodiment, the spoked body of the plunger and flange are of integral construction, while the resilient piston 30 is secured to the plunger body in a conventional manner. However, it is within the purview of the instant invention to include one piece plungers wherein the piston is integrally formed with the plunger of the same material, or different materials such as by two-color molding.

Figure 4:
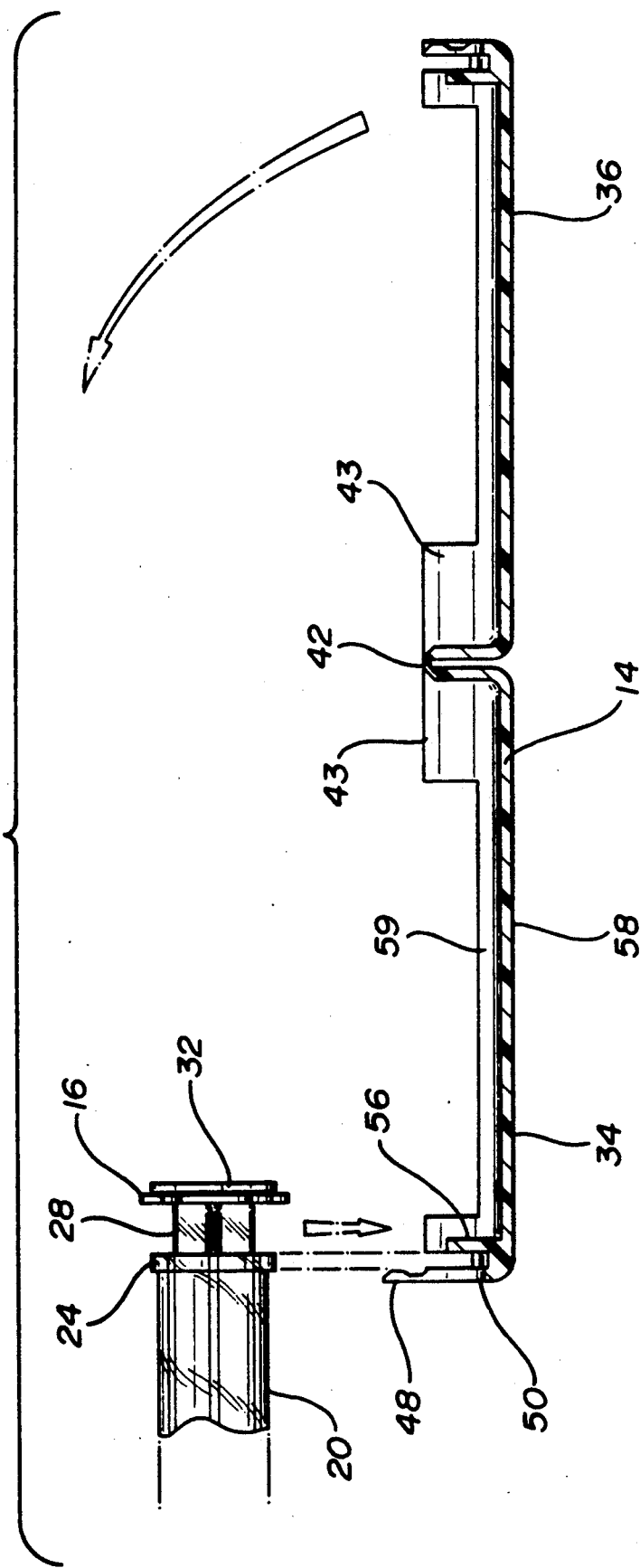
FIG. 4 is an exploded, sectional side elevation view illustrating the mounting of an adapter to a syringe.
Figure 5:
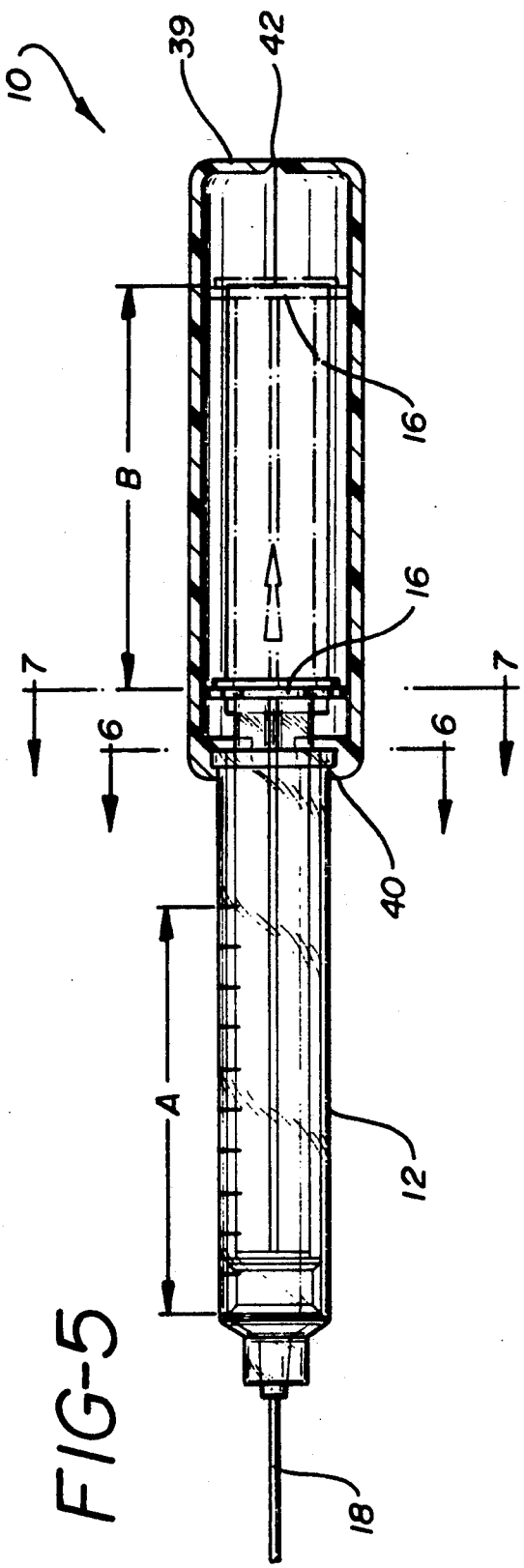
FIG. 5 is a partial cross sectional view taken along line 5—5 of FIG. 2.
Figure 10:
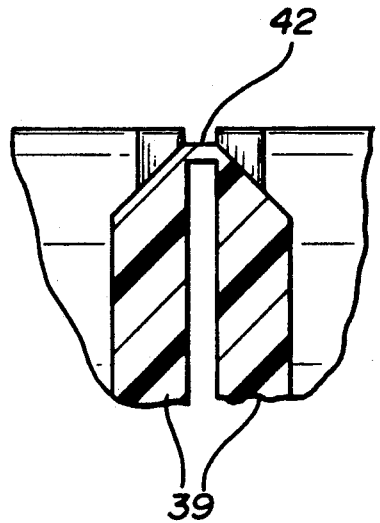
FIG. 10 is an enlarged fragmentary view of the hinged section of the adapter in an open position.
Figure 11:
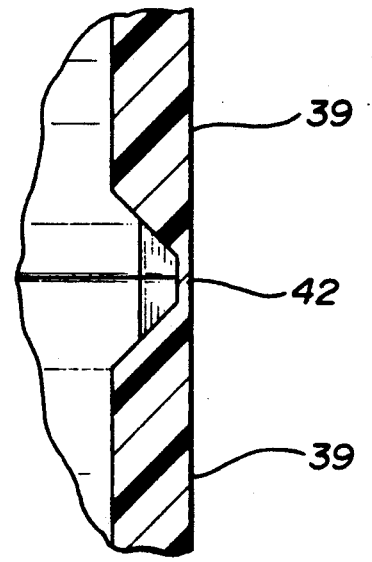
FIG. 11 is an enlarged fragmentary view of the hinged section of the adapter in a closed position.

The adapter 14 includes an elongate, generally cylindrical body portion comprising first and second elongate members 34, 36, a first proximal end portion 38, and a second distal end portion 40. The first end portion 38 is integrally molded with the elongate members. It includes an end wall 39 including a living hinge 42 which allows the elongate members 34, 36 to be pivoted about said living hinge between an open position as shown in FIGS. 3 and 4 and a closed position as shown in FIGS. 1, 2 and 5. FIGS. 10 and 11 show the hinge 42 in the open and closed positions, respectively.

It is within the purview of this invention to include means other than a hinge to secure elongate members 34 and 36 together such as cooperating surfaces to lock members 34 and 36 together in a snap fit arrangement or through the use of adhesive or other joining means such as ultrasonic welding and the like. The hinged wall 39 is oriented substantially perpendicularly with respect to the longitudinal axis of the adapter when the adapter is in the closed position. The longitudinal axis of the adapter is substantially parallel to the longitudinal axis of the syringe barrel to which the adapter is secured. The two axes may, in fact, be substantially colinear. A pair of arcuate sides walls 43 adjoin the hinged end wall 39.

The second end portion 40 of the adapter includes two halves, each half including a pair of opposing side walls 44 having slots 46 therein. The slots 46 within each half are in opposing relation. When the adapter is in the closed position, the slots of the first half are aligned with those of the second half and the side walls 44 are adjacent to each other.

Figure 9:
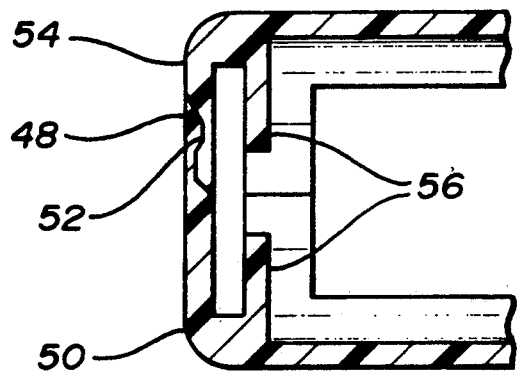
FIG. 9 is an enlarged fragmentary view of the front end of the syringe adapter with the syringe removed for clarity.

Preferably adapter 14 includes means for releasably securing the first half of the second distal end portion 40 to the second half thereof. Such means include a pair of projections 48 extending from an end wall 50 of the first half and a pair of grooves 52 cut into an end wall 54 of the second half. The projections lock within the grooves when the adapter is in the closed position, as best shown in FIG. 9. They are released by slightly deforming the first or second half of the adapter and then urging the two halves apart.

It is within the purview of the present invention to include embodiments having means for securing the halves of distal end portion 40 which are not releasable. Permanent attachment of the adapter will identify the syringe as a sample collecting or biopsy instrument and help prevent accidental reuse for injection purposes.

Each half of the second end portion 40 of the adapter includes a radially inwardly extending wall 56 positioned in opposing relation to and a selected distance from the respective end walls 50, 54 thereof. This distance corresponds approximately to the thickness of the flanges 24 of the syringe barrel 20.

Figure 7:
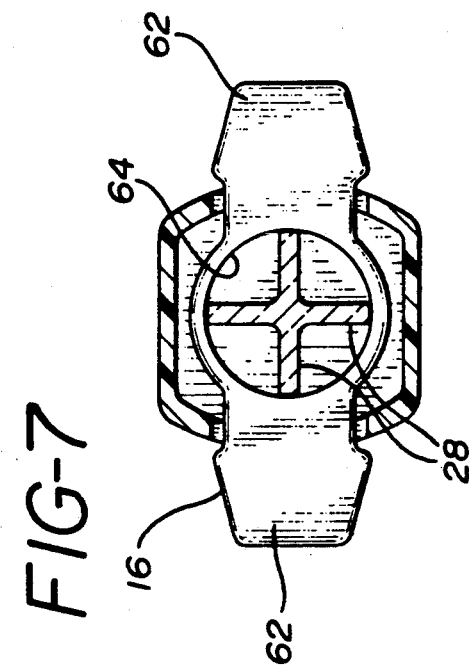
FIG. 7 is an enlarged cross-sectional view taken along line 7—7 of FIG. 5.
Figure 6:
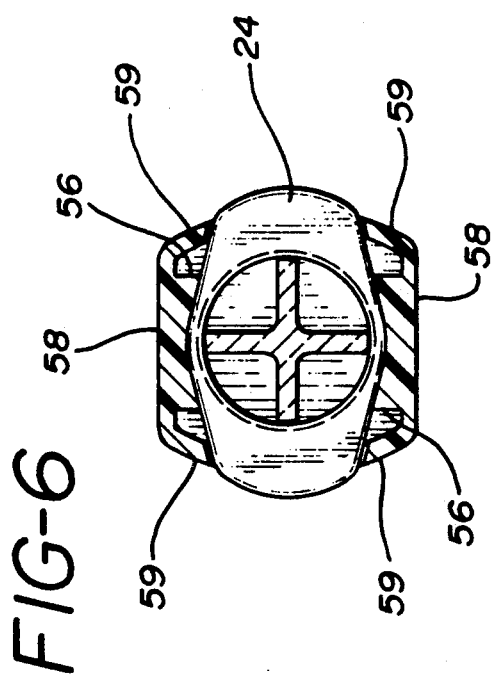
FIG. 6 is an enlarged cross sectional view taken along line 6—6 of FIG. 5.

The elongate members 34, 36 which comprise the body portion of the adapter 14 each include a substantially flat wall 58 and a pair of adjoining side walls 59. Each side wall 59 is arcuate in cross section, as shown in FIGS. 6 and 7. In addition, the side walls 59 are shorter in height than the side walls 43, 44 of the first and second end portions 38, 40, respectively. A pair of opposing, elongate slots 60 are accordingly defined by the side walls 43, 44, 59 when the adapter is in the closed position.

Figure 8:
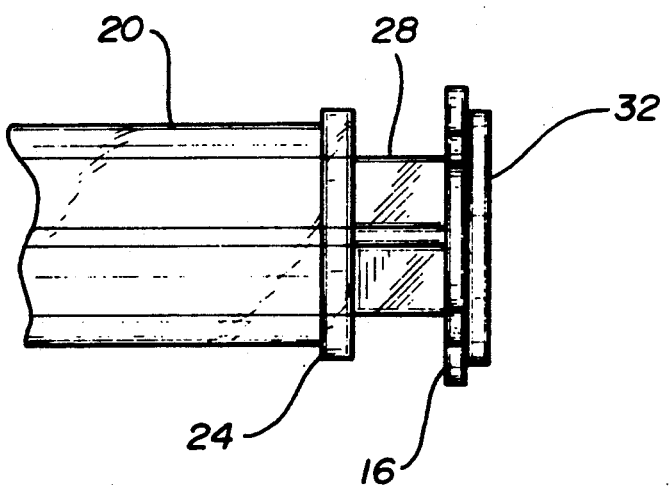
FIG. 8 is an enlarged side elevation view of the rear end of the syringe assembly with the winged member attached.

The winged member 16 includes a pair of radially projecting flanges 62 and an opening 64 extending therethrough. As shown in FIGS. 7 and 8, the spoked portion of the plunger 28 extends through the opening 64.

The winged member abuts against the flange 32 which defines the thumb pad of the syringe plunger 28. It converts the plunger from a component which is pushed to one which may easily be pulled via the flanges 62. The winged member may be bonded to the plunger to provide a more secure assembly. This may be accomplished by welding, applying epoxy between the flange 32 and winged member 16, or other suitable method such as mechanical joining through an interference or snap fit. Also, it is within the purview of the instant invention to include wings integrally formed with the plunger. An important feature of the instant invention is that the flange or like structure such as the winged member on the plunger rod is large enough to project sufficiently outwardly from the adapter to allow one handed operation of the assembly for drawing a sample of tissue or fluid into the barrel.

The adapter 14 and winged member 16 are used to convert a syringe 12 from a device best suited for injecting a fluid to an assembly 10 which can be used for aspirating a fluid using only one hand. The winged member 16 is first pushed over the syringe plunger 28 until it engages the flange 32 thereof. It then may be attached thereto using adhesive or mechanical means or even remain there. The plunger 28 is then inserted within the syringe barrel 20.

The syringe 12, now including the winged member 16, is positioned over the open adapter 14. The flat walls 56 of the adapter allow it to be positioned on a flat surface without rolling. The syringe 12 is then placed upon the adapter such that the flanges 24 at the rear end of the syringe barrel 20 are positioned within the opposing slots 46 of one half of the second end portion 40 of the adapter. Upon closing the adapter, the flanges 24 are locked in position by the slots 46. The end walls 50, 54 of the second end portion 40 and inwardly extending walls 56 also serve to lock the smaller portions of the flanges 24 in position, as shown in FIG. 5.

The flanges 62 of the winged member 16 extend outside the adapter through the opposing slots 60 of the closed adapter. The slots are preferably long enough to permit a full range of motion of the piston 30 within the syringe barrel 20.

The projections 48 extending from end wall 50 of the adapter fit within the grooves 52 in the end wall 54. The outside surfaces of the projections are substantially coplanar with the adjoining end walls 50, 54. These end walls define a circular opening through which the syringe barrel extends.

Once the adapter is locked in the closed position, the user urges the winged member 16 toward the front end of the adapter 14 until the piston 30 engages the front end of the syringe barrel 20. Once the needle 28 has been inserted into the body or other source of fluid or tissue, the plunger 28 may be retracted through the use of only one hand. The index and middle fingers of the one hand engage the flanges 62 of the winged member while the thumb thereof is applied against the rear wall 39 of the adapter. The winged member 16, and therefore the piston 30 and plunger 28, are retracted in this manner. Tissue or fluid is accordingly aspirated into the needle 18 and, in some cases, into the syringe barrel 20.

If the winged member is bonded to the plunger flange 32, the barrel contents may be expelled by urging the flanges 62 in the opposite direction. Otherwise the user would simply disengage the projections 48 from the grooves 52 and remove the adapter 14 before urging the plunger 28 toward the needle 18. The flange 32 would serve as a thumb pad in the latter procedure.

Figure 12:
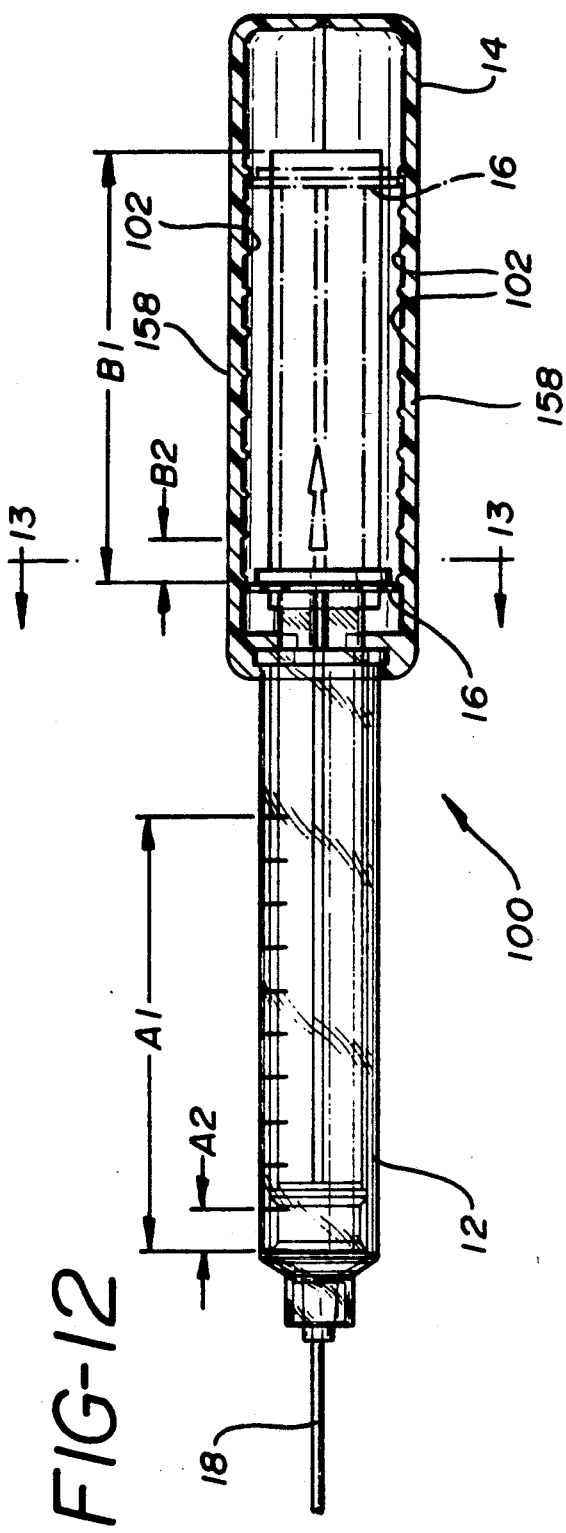
FIG. 12 is a cross-sectional view of an alternative embodiment of the invention with a ratchet mechanism.
Figure 13:
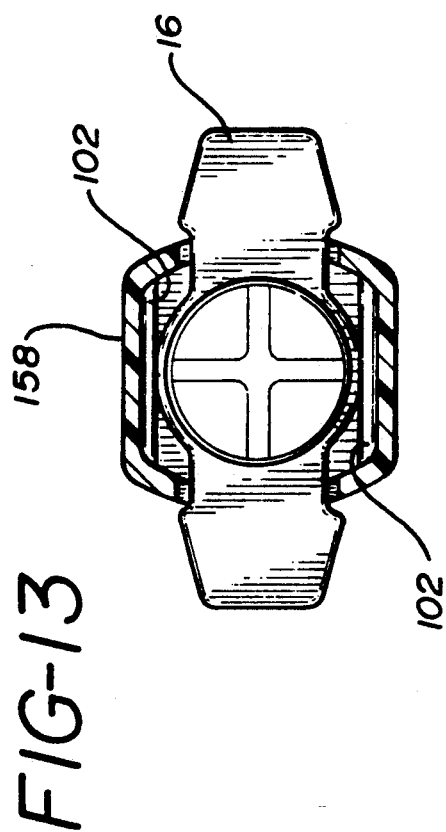
FIG. 13 is an enlarged cross sectional view taken along line 13—13 of FIG. 12.

Referring to FIGS. 12-13, an alternative embodiment of the invention is shown which allows the syringe plunger 28 to be locked into discrete positions. A desired negative pressure within the syringe barrel 20 may accordingly be maintained.

The assembly 100 includes a syringe 12, winged member 16 and needle 18 which are identical to those shown in FIG. 1. It also includes an adapter 114 which is substantially the same as the abovementioned adapter 14, but also includes a ratchet mechanism designed to interlock with the winged member 16 or the flange 32 of the syringe plunger 28 whichever is of greater diameter. This interlocking relationship can be accomplished using a wall projecting from the winged member, the flange or other portion of the plunger to interact as part of the ratchet mechanism. The ratchet mechanism includes a pair of opposing rows of teeth 102 extending inwardly from the flat top and bottom walls 158 of the adapter 114. Each row of teeth may be spaced apart by a distance corresponding to the distance between each graduation line on the syringe barrel. Other spacings could alternatively be employed. When the winged member 16 is moved behind a pair of opposing teeth 102, a vacuum is created in the syringe barrel. The vacuum is maintained until a desired volume of fluid or tissue enters the syringe barrel or the needle. The interaction between the winged member and the projections helps prevent distal motion of the plunger when the barrel is partially evacuated due to manually induced proximal motion of the plunger when collecting samples through the needle.

It is also within the purview of the instant invention to include structure to allow at least one row of projections to be moved or pivoted out of the path of the winged member to reduce or eliminate the resistance to plunger motion caused by the projections.

Although illustrative embodiments of the present invention have been described herein with the reference to the accompanying drawings, it is to be understood that the invention is not limited to those precise embodiments, and that various other changes and modifications may be effected therein by one skilled in the art without departing from the scope or spirit of the invention.

What is claimed is:

1. An adapter for attachment to a syringe having a barrel including a distal end, a tip on said distal end, a proximal end, a flange on said proximal end, a piston positioned in said barrel, a plunger projecting proximally outwardly from said barrel and a radially projecting flange on the proximal end of said plunger comprising:

a body portion including first and second elongate members, and means for securing said first and second elongate members to each other including a hinge at said first end portion, at least one of said first and second elongate members being pivotable about said hinge.

said body portion having a longitudinal axis including a first proximal end portion having an exterior end surface and a second distal end portion, opposite said proximal end portion, said second end portion including means for engaging the flange of said syringe barrel so that the distal end of said syringe barrel extends outwardly from said second end portion and said plunger is positioned at least partially within said body portion; and access means in said body portion for allowing access to the flange of said plunger so that said plunger can be withdrawn with one hand by causing one or more fingers to exert pressure on said flange of said plunger in a direction of said exterior end surface while the thumb engages said exterior end surface.

2. An adapter as described in claim 1 wherein said access means includes a pair of opposed elongate slots extending substantially parallel to said longitudinal axis of said body portion.

3. An adapter as described in claim 1 wherein said first and second elongate members define a generally cylindrical construction.

4. An adapter as described in claim 1 wherein said body portion includes a row of projections positioned substantially perpendicular to said longitudinal axis of said body portion, each of said projections extending toward said longitudinal axis of said body portion for releasably engaging said plunger to help prevent distal motion of said plunger when said syringe barrel is partially evacuated.

5. An adapter as described in claim 1 wherein said means for securing said first and said second elongate member to each other includes means for locking said first elongate member in a fixed position with respect to said second elongate member.

6. An adapter as described in claim 5 wherein said means for locking is defined by said second end portion.

7. An adapter as described in claim 5 wherein said locking means irreleasably secures said elongate members to each other and to the syringe barrel.

8. An adapter as described in claim 5 wherein said first and second elongate members and said first and second end portions are of integral construction.

9. An adapter as described in claim 8 wherein said first end portion includes a living hinge.

* * * * *